US 6,703,398 B2

(12) United States Patent
Hu et al.

(10) Patent No.: US 6,703,398 B2
(45) Date of Patent: Mar. 9, 2004

(54) ORALLY ADMINISTERED ANALGESIC COMPOSITIONS CONTAINING NALBUPHINE

(75) Inventors: Oliver Yoa-Pu Hu, 2F, No. 81, Alley 5, Lane 24, Sec. 3, Ting-Chou Road, Taipei (TW); Cheng-Huei Hsiong, Taipei (TW)

(73) Assignee: Oliver Yoa-Pu Hu, Taipei (TW)

( * ) Notice: Subject to any disclaimer, the term of this patent is extended or adjusted under 35 U.S.C. 154(b) by 0 days.

(21) Appl. No.: 09/991,948

(22) Filed: Nov. 26, 2001

(65) Prior Publication Data

US 2003/0105120 A1 Jun. 5, 2003

(51) Int. Cl.⁷ .................. A61K 31/485; A61K 31/473; A61K 31/20
(52) U.S. Cl. .................. 514/282; 514/279; 514/558
(58) Field of Search ............... 514/282, 279, 514/558; 424/445, 448, 449

(56) References Cited

U.S. PATENT DOCUMENTS

| 4,626,539 A | * | 12/1986 | Aungst et al. ............... 514/282 |
| 4,673,679 A | * | 6/1987 | Aungst et al. ............... 514/282 |
| 5,156,835 A | * | 10/1992 | Nabi et al. ..................... 426/52 |
| 5,294,431 A | * | 3/1994 | Gaffar et al. .................. 424/49 |
| 5,750,534 A | | 5/1998 | Yoa-Pu et al. |
| 6,225,321 B1 | | 5/2001 | Hu et al. |
| 6,455,066 B1 | * | 9/2002 | Fischer et al. ............... 424/449 |

OTHER PUBLICATIONS

S. Sabnis; Factors Influencing the Bioavailability of Peroral Formulations of Drugs for Dogs; Veterinary Research Communications, 1999, P 425–447, vol. 23; Kluwer Academic Publishers, Netherlands.

J. Zuidema et al.; Release and absorption rates of intramuscularly and subcutaneously injected pharmaceuticals (II); International Journal of Pharmaceutics, 1994, P 189–207, vol. 105; Elsevier Science B.V.

M.K. Al–Hindawi et al.; Influence of solvent on the availability of testosterone propionate from oily, intramuscular injections in the rat; J. Pharm. Pharmacol, 1987, P 90–95, vol. 39.

Jane Croft Harrelson et al.; Species variation in the disposition of nalbuphine and its acetylsalicylate ester analogue; Xenobiotica, 1988, P 1239–1247, vol. 18, No. 11.

* cited by examiner

Primary Examiner—Zohreh Fay
Assistant Examiner—Brian-Yong S. Kwon
(74) Attorney, Agent, or Firm—Fei-Fei Chao; Venable LLP

(57) ABSTRACT

The present invention provides orally administered pharmaceutical compositions which contains an effective amount of free base or pharmaceutcially acceptable salts of nalbuphine and/or nalbuphine ester, an oily substance, and a solubility-assisting agent. The oily substance is preferably sesame oil. The solubility-assisting agent is preferably benzyl benzoate. The pharmaceutical composition is useful as an analgesic. The compositions achieves a much higher bioavailability rate and yields much longer lasting effects on nalbuphine than other nalbuphine products currently in the market.

14 Claims, 1 Drawing Sheet ent carbon numbers resulting in an increase in lipophilicity of the prodrugs. When the prodrugs are given intramuscularly, the release rates are decreased and the duration of action is prolonged. Ester-type prodrugs are hydrolyzed by esterases in the body to yield increase of mother compounds in vivo. Esterases exist in many tissues and organs including blood, liver, heart, brain, kidneys, lungs, and muscles. The pharmacological effect and safety of the ester type prodrug and the mother compound are reported to be the same.

ORALLY ADMINISTERED ANALGESIC COMPOSITIONS CONTAINING NALBUPHINE

FIELD OF THE INVENTION

The present invention relates to novel analgesic pharmaceutical compositions containing free base or pharmaceutically acceptable salts of nalbuphine and/or nalbuphine ester, an oily substance, and a solubility-assisting agent. In particular, the present invention relates to orally administered nalbuphine and/or nalbuphine ester which demonstrates long lasting effect and greater bioavailability for pain relief in animals. The preferred oily substance is sesame oil. The preferred solubility-assisting agent is benzyl benzoate.

BACKGROUND OF THE INVENTION

Nalbuphine is a synthetic opiate agonist-antagonist that is chemically related to both naloxone, a narcotic antagonist, and oxymorphone, a potent narcotic analgesic. Nalbuphine simultaneously exhibits a dual action of agonism and antagonism towards opioids-receptors. Schmidt, W. F. et al., *Drug Alcohol Depend.*, Vol. 14, page 339 (1985). Opiate receptors include mu, kappa, and delta, which have been reclassified by an International Union of Pharmacology subcommittee as OP1 (delta), OP2 (kappa), and OP3 (mu). Nalbuphine acts on specific opiate-receptor subtypes: it is a potent mu-antagonist with less dysphoric effects, and its agonistic effects at kappa1- and kappa3-receptors provide analgesia.

Actions of nalbuphine at the kappa-receptors produce alterations in the perception of pain as well as the emotional response to pain, possibly by altering the release of neurotransmitters from afferent nerves sensitive to painful stimuli. As an adjunct to anesthesia, nalbuphine protects against the hemodynamic responses to stress produced by surgery. Additionally, nalbuphine paradoxically produces opiate withdrawal if administered to opiate-dependent patients, which is a function of antagonism at the mu-receptor. Stimulation at mu-receptor produces respiratory depression. However, nalbuphine causes less respiratory depression than morphine or related agents.

Nalbuphine is used to treat moderate to severe pain associated with acute and chronic medical disorders such as cancer, renal or biliary colic, migraine or vascular headaches, and surgical pain. Nalbuphine is effective in control of severe and deep pain caused by cardiac, pulmonary, abdominal, osteopathia, and obstetrical surgery, severe burn injury, and the terminal stages of cancer via various administration routes, such as intramuscular, intravenous, intrathecal. The FDA approved nalbuphine in 1979.

Compared with conventional analgesics, nalbuphine drastically reduces induction of addiction and accretion of dosage in patients. In addition, Nalbuphine has decreased inhibition on respiratory system. Some evidence suggests that nalbuphine depressant effects on the respiratory system do not increase proportionately with increasing doses, which makes the drug safer in patients at risk from respiratory depression. However, the duration of Nalbuphine action is short, which is not enough to relieve the severe pain.

Broekkamp et al., J. Pharm. Pharmacol., Vol. 40, 434 (1988), proposes a long-acting mechanism by ester-type prodrugs. The drugs are esterified with fatty acids of different carbon numbers resulting in an increase in lipophilicity of the prodrugs. When the prodrugs are given Additionally, the conventional form of nalbuphine, nalbuphine hydrochloride (nalbuphine-HCl), is not practical for oral administration, because the bioavailability through oral administration is less than 5%. Thus, nalbuphine-HCl has not been made available in a form for oral administration. In a paper published in 1988 by Harrelson J. C. and Wong Y. J., *Xenobiotica* (1988), 18:1239–1247, the researchers found that acetylsalicylate ester prodrug of nalbuphine improved the bioavailability through oral administration, which also masked the bitter taste of nalbuphine-HCl. However, the bioavailability of the acetylsalicylate ester prodrug is only 16%, which is still not effective enough for oral administration. In another paper published in 1988 by Hussain, M. A. et al., J. Pharm. Sciences, 75:218–219 (1986), the researchers found that buccal delivery could improve the bioavailability of the opioids prodrugs to as high as 35–50%. Nevertheless, buccal delivery is not as convenient and acceptable as oral administration. Therefore, pharmaceutical compositions containing nalbuphine base with long-acting effects and high bioavailability for oral administration are desirable.

Recently, Yoa-Pu et al., U.S. Pat. No. 5,750,534 (the '534 patent), disclose a nalbuphine prodrug which contains nalbuphine monoester, wherein the R in the ester group (RCO) is a straight or branched alkyl group of 2–36 carbon atoms or a phenyl group. The nalbuphine monoester prodrug is characterized as having prolonged analgesic duration. The '534 patent is herein incorporated by reference.

Hu et al., U.S. Pat. No. 6,225,321 (the '321 patent), disclose yet another nalbuphine prodrug which contains nalbuphine polyester having a generic formula of R—[CO—NAL]$_n$, wherein n is an integer from 2–4 and R in the ester group is a saturated or nonosaturated, substituted or unsubstituted, aliphatic or aromatic group having 1 to 40 carbon atoms. The nalbuphine polyester is designed as a soft drug which can maintain analgesic effect in animal body for 4–5 days. The '321 patent is herein incorporated by reference.

In the sections to be presented below, the present invention provides a pharmaceutical composition which, by incorporating the nalbuphine ester prodrugs as described in the '534 patent and the '321 patent as the active ingredient, together with an oily substance and a solubility-assisting agent, can be administered orally. The pharmaceutical composition of the present invention not only provides long-lasting effect but also demonstrates greater bioavailability for pain relief in animal body.

SUMMARY OF THE INVENTION

The present invention provides pharmaceutical compositions which contain (1) an active ingredient, which is a nalbuphine or a nalbuphine ester prodrug, or the pharmaceutically acceptable salts of nalbuphine or nalbuphine ester prodrug; (2) an oily substance, and (3) a solubility-assisting agent. The pharmaceutical composition is preferably administered orally.

There are two kinds of nalbuphine ester prodrugs, which are nalbuphine monoester and nalbuphine polyester.

Examples of nalbuphine monoester include, but are not limited to, nalbuphine propionate, nalbuphine pivalate, nalbuphine enanthate, nalbuphine decanoate, nalbuphine behenate, nalbuphine erucicate, nalbuphine arachidate, and nalbuphine benzoate. Examples of nalbuphine polyester include, but are not limited to, adipoyl dinalbuphine ester, sebacoyl dinalbuphine ester, 1,3-cyclohexane diacid dinalbuphine ester, docosanodic dinalbuphine ester, 3,3-dimethylglutaric diacid dinalbuphine ester, trinalbuphine trimesoyl ester, 1,3,5-cyclohexane triacid trinalbuphine ester, pyromellitoyl tetranalbuphine ester. Among the nalbuphine ester prodrugs, sebacoyl dinalbuphine ester (SDN) is the most preferable one to be used in oral administration.

The oily substance is preferably a vegetable oil, and more favorably sesame oil, soybean oil or peanut oil. The most favorable vegetable oil is sesame oil. The solubility-assisting agent is preferably benzyl benzoate.

The pharmaceutical composition of the present invention contains about 1% to 15% by weight of free base or salts of nalbuphine or nalbuphine ester prodrug, preferably about 10% by weight; about 30% to 90% by weight of the oily substance, preferably about 55% by weight of sesame oil; and about 5% to 50% by weight of the solubility-assisting agent, preferably about 45% by weight of the solubility-assisting agent.

The present invention also provides a method for treating patients with severe, long lasting pain by orally administering the pharmaceutical composition described above to patients. The severe, long lasting pain suffered by patients is caused by cardiac, pulmonary, osteopathia, obstetrical surgery, burn injury, or terminal stage of cancer.

The nalbuphine ester prodrug-containing oral pharmaceutical composition demonstrates high bioavailability in vivo and prolong pain-killing effect. Also, because the pharmaceutical composition provided in the present invention can be administered orally, it is more convenient than the traditional use of nalbuphine, i.e., by injection or buccal delivery.

DETAILED DESCRIPTION OF THE INVENTION

Figure 1:
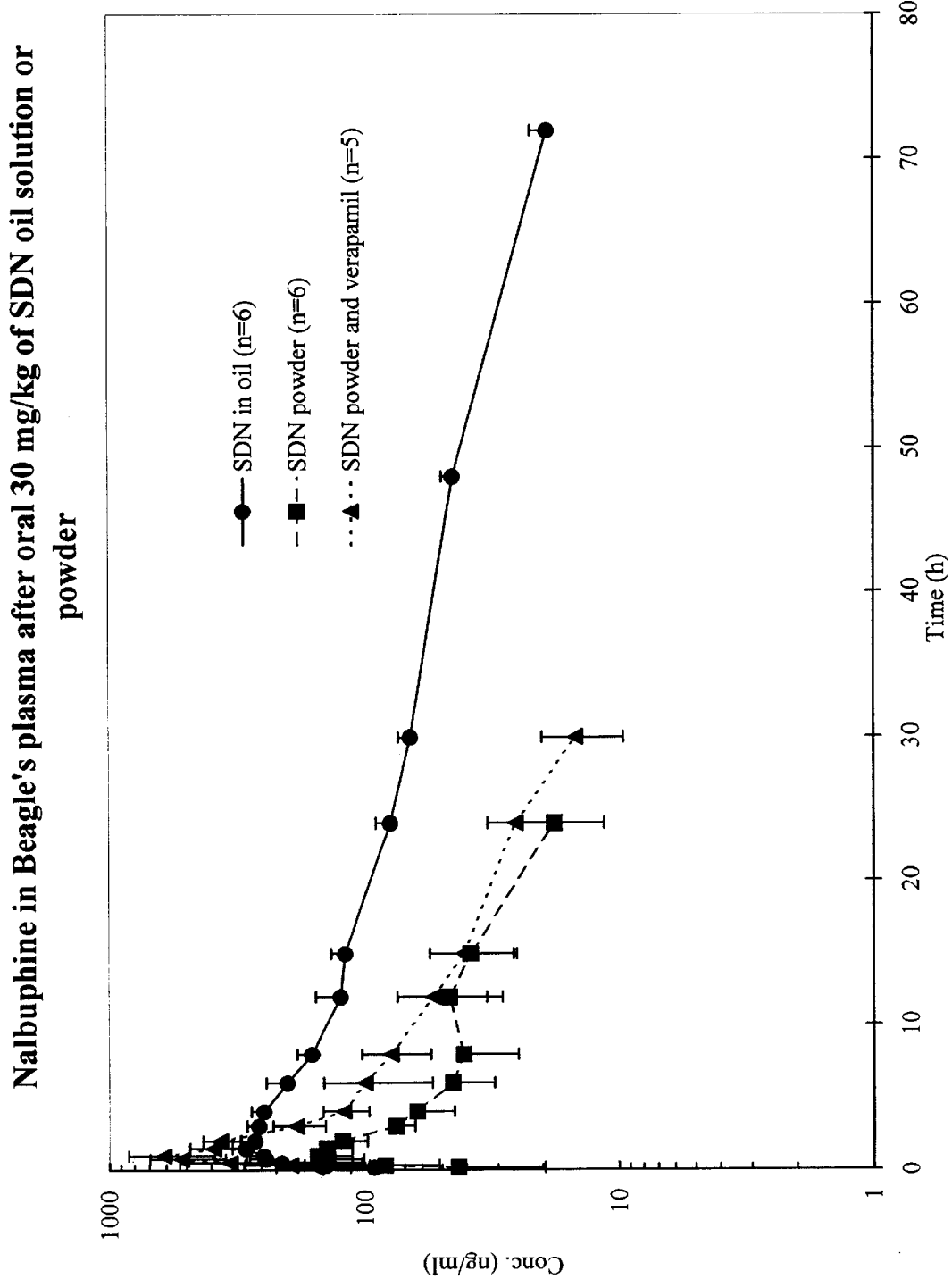
FIG. 1 shows the nalbuphine concentration in blood plasma in beagles after the pharmaceutical compositions were orally administered into the animals. ●--● represents the group of animals (n=6) which were given the pharmaceutical composition containing (1) SDN, (2) sesame oil, and (3) benzyl benzoate; ■--■ represents the group of animals (n=6) which were given the pharmaceutical composition containing SDN powder only; ▲--▲ represents the group of animals which were given the pharmaceutical composition containing SDN plus verapmail (n=6).

The present invention provides an oral pharmaceutical composition which contains an effective amount of nalbuphine, nalbuphine derivatives, or pharmaceutically acceptable nalbuphine salts thereof.

Nalbuphine is a morphine derivative. Nalbuphine has the chemical formula (I):

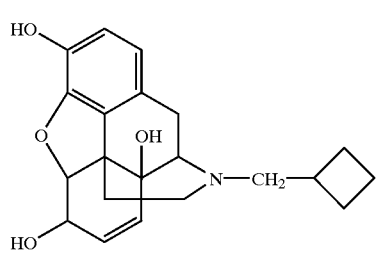

Formula (I)

A nalbuphine monoester prodrug has the following generic chemical formula (II):

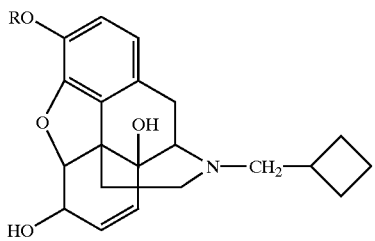

Formula (II)

in which R is R'CO, wherien R' is a straight or branched alkyl group of 2–36 carbon atoms or a phenyl group. (Yoa-Pu et al., U.S. Pat. No. 5,750,534).

The preferred nalbuphine monoester prodrugs which include, but are not limited to, nalbuphine propionate, nalbuphine pivalate, nalbuphine enanthate, nalbuphine decanoate, nalbuphine behenate, nalbuphine erucicate, nalbuphine arachidate, and nalbuphine benzoate.

A nalbuphine polyester prodrug has the following generic chemical formula (III):

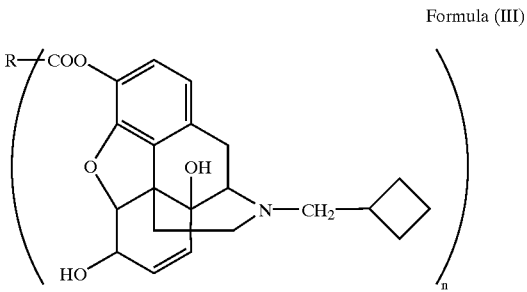

Formula (III)

wherein n is an integer from 2 to 4 and wherein R is a saturated or unsaturated, substituted or unsubstituted, aliphatic or aromatic group having 1 to 40 carbon atoms. (Hu et al., U.S. Pat. No. 6,225,321).

The preferred nalbuphine polyester prodrugs include adipoyl dinalbuphine ester, sebacoyl dinalbuphine ester, 1,3-cyclohexane diacid dinalbuphine ester, docosanodic dinalbuphine ester, 3,3-dimethylglutaric diacid dinalbuphine ester, trinalbuphine trimesoyl ester, 1,3,5-cyclohexane triacid trinalbuphine ester, pyromellitoyl tetranalbuphine ester. The most favorable nalbuphine polyester prodrug is sebacoyl dinalbuphine ester (SDN).

The pharmaceutical composition of the present invention contains three major components: (1) an active ingredient; (2) an oily substance; and (3) a solubility-assisting agent.

The active ingredient of the pharmaceutical composition includes nalbuphine, nalbuphine monoester, and nalbuphine polyester, or a pharmaceutically acceptable salts of nalbuphine, nalbuphine monoester, and nalbuphine polyester. The preferred active ingredient is nalbuphine polyester. Among nalbuphine polyester, the most favorable one is sebacoyl dinalbuphine ester.

The amount of nalbuphine or nalbuphine ester prodrug used in the pharmaceutical composition of the present invention is about 1% to 15% by weight of the composition. The preferred concentration of sebacoyl dinalbuphine ester in the pharmaceutical composition of the present invention is 100 mg/ml.

The oily substance in the pharmaceutical composition of the present invention includes a vegetable oil. The vegetable oil used in the present invention include, but are not limited to, sesame oil, soybean oil, peanut oil, or an ethyl ester of sesame oil, soybean oil, or peanut oil. The preferred oily substance is sesame oil. The pharmaceutical composition contains about 30% to 90% by weight of vegetable oil.

The solubility-assisting agent of the pharmaceutical composition is benzyl benzoate. The pharmaceutical composition contains about 5% to 50% by weight of the solubility-assisting agent.

Each and every one of these nalbuphine and/or nalbuphine ester prodrugs as listed above has been tested for suitability as an orally administered pharmaceutical composition for use in animals and humans. The efficacy and bioavailability of these nalbuphine ester prodrugs have been studied. The results indicate that the addition of the solubility-assisting agent to the nalbuphine and/or nalbuphine ester prodrugs and an oily substance substantially improves the bioavailability and half-life of nalbuphine in blood.

Among the nalbuphine active ingredient, sebacoyl dinalbuphine ester (SDN) appears to be the best in terms of longer half-life and greater bioavailability rate. The studies using SDN as an example are therefore provided below. Please note that the following examples are illustrative only, and should not be viewed as limiting the scope of the present invention. Reasonable variations, such as those occur to reasonable artisan, can be made herein without departing from the scope of the present invention.

EXAMPLE 1

Preparation of the Pharmaceutical Composition

The pharmaceutical composition of the present invention is prepared as follows:

1. Mixing 5.5 ml sesame oil with 4.5 ml benzyl benzoate and stirring well to form an oily mixture.

2. Adding 1 g of SDN to 10 ml of the oily mixture with further stirring to produce a homogeneous pharmaceutical composition containing about 100 mg SDN per ml of the oily mixture.

EXAMPLE 2

Comparative Studies of the Pharmaceutical Compositions in Beagles

Purpose

To assess the effects of various pharmaceutical compositions of the present invention on beagles. The compositions were orally administered into beagles, and the concentration of nalbuphine in vivo was monitored in the animals as follows:

Method

1. Three pharmaceutical compositions were tested in this study, which include: (1) the pharmaceutical composition described in EXAMPLE 1 (the "Complete SDN" group); (2) pure sebacoyl dinalbuphine ester powder without any oily substance or solubility-assisting agent (the "SDN Powder" group); and (3) sebacoyl dinalbuphine ester with verapamil (which is used as an oily substance) (the "SDN+Verapamil" group).

2, In each study group, the pharmaceutical composition that contained 30 mg/kg of SDN were orally given to beagles.

3. Blood samples were taken from the forearm vein at 0.167, 0.33, 0.5, 0.75, 1, 1.5, 2, 3, 4, 6, 8, 12, 15, 24, 30, and 48 hours after the oral administration.

4. The blood samples were analyzed by high performance liquid chromatography (HPLC) to determine the pharmacokinetics (including the half-life and bioavailability of nalbuphine) in vivo.

Result

As shown in FIG. 1, the concentration of nalbuphine in the three groups peaked about 1–2 hours after oral administration of the pharmaceutical compositions. Among the three groups, both the Complete SDN group and the SDN+Verapamil group had about the same concentration of nalbuphine in plasma 1–3 hours after the oral uptake of SDN. The concentration of nalbuphine in the SDN powder was much less than the other two groups. However, the concentration of nalbuphine in the SDN powder and the SDN+verapamil group decreased substantially whereas the concentration of nalbuphine in the Complete SDN group still maintained at high percentage.

Verapamil is α-[3-[[2-(3,4-dimethoxyphenyl)ethyl] methylamino]propyl]-3,4-dimethoxy-α-(1-methylethyl)-benzeneacetonitrile. It is a viscous, pale yellow oil. Verapamil is a well-known cytochrome $P_{450}$ 3A (CYP 3A) inhibitor.

CYP 3A is known to be responsible for metabolism of a large number of drugs in vivo, thus, reducing the bioavailability of drugs. The drugs that are know to be affected by CYP 3A include nifedipine, macrofide antibiotics such as erythromycin and troleandomycin, cyclosporin, FK506, teffenadine, tamoxifen, lidocaine, midazolam, triazolam, dapsone, diltiazem, lovastatin, quinidine, ethylestradiol, testosterone, and alfentanil. A CYP 3A inhibitor can be used to inhibit the enzymatic activity of CYP 3A and thus improve the bioavailability of the drugs.

Assuming that the bioavailability of nalbupine is also affected by CYP 3A, an inclusion of verapamil (the CYP 3A inhibitor), together with SDN, should further improve the bioavailability of nalbupine (if there is an synergistic effect between verapamil and SDN).

The results in FIG. 1 suggest that without the solubility-assisting agent (benzyl benzoate), the addition of verapamil did not improve the bioavailability of nalbupine.

Table 1 shows the results of the pharmacokinetic studies of the three pharmaceutical compositions.

TABLE 1

Pharmacokinetics of Nalbuphine in Beagles

| Nalbuphine Pharmcokinetics | Complete SDN Group | SDN Powder Group | SDN + Verapamil Group |
| --- | --- | --- | --- |
| Nalbuphine Half-Life (hrs) | 23.9 ± 3.0 | 8.1 ± 1.6 | 9.5 ± 2.3 |
| AUC/Dose (h*ng*kg/ml/mg) | 171 ± 18 | 39 ± 11 | 83 ± 22 |
| Bioavailability (%) | 67.1 ± 4.3 | 14.6 ± 4.0 | 30.0 ± 8.0 |

*Data = means ± S.E.

As shown in Table 1, the nalbuphine half-life ($t_{1/2}$) in the Complete SDN group is 23.9±3.0 hours, which was about 3 times longer than that of the SDN powder group and about 2.5 times longer than that of the SDN+Verapamil group. The bioavailability of nalbuphine, as determined by AUC (area under curve) and by % of decrease (% bioavailability) also shows that the Complete group is far much better than the rest of the two group (AUC-171[Complete Group] vs. 39 [SDN Powder Group] or 83 [SDN+Verapamil Group]; % bioavailability: 67% [Complete Group] vs. 14.6 [SDN Powder Group] or 30.0 [SDN+Verapamil Group]).

The results of FIG. 1 and Table 1 show that the addition of an oily substance to SDN greatly improve the half-life and bioavailability of nalbuphine in plasma (as comparing the SDN Powder Group and SDN+verapamil Group). But the half-life and bioavailability rate of nalbuphine is far much greater when benzyl benzoate as a solubility-assisting agent is added to SDN with oil (as comparing the Complete SDN Group with the SDN Powder Group and SDN+verapamil Group).

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A pharmaceutical composition consisting essentially of as an active ingredient, an effective amount of free base or pharmaceutically acceptable salts of nalbuphine or nalbuphine ester;

an oily substance; and an agent for improving bioavailabliity and half-life of said free base or pharmaceutically acceptable salts of nalbuphine or nalbuphine ester in blood; wherein said agent is benzyl benzoate;

wherein said pharmaceutical composition is an orally administered composition.

2. The pharmaceutical composition according to claim 1, wherein said nalbuphine ester is nalbuphine monoester or nalbuphine polyester.

3. The pharmaceutical composition according to claim 2, wherein said nalbuphine monoester is at least one selected from the group consisting of nalbuphine propionate, nalbuphine pivalate, nalbuphine enanthate, nalbuphine decanoate, nalbuphine erucicate, nalbuphine arachidate, and nalbuphine banzoate.

4. The pharmaceutical composition according to claim 2, wherein said nalbuphine polyester is at least one selected from the group consisting of adipoly dinalbuphine ester, sebacoyl dinalbuphine ester, 1,3-cyclohexane diacid dinalbuphine ester, docosanodic dinalbuphine ester, 3,3-dimethylgiutaric diacid dinalbuphine ester, trinalbuphine trimesoyl ester, 1,3,5-cyclohexane triacid trinalbuphine ester, and pyromellitoyl tetranalbuphine ester.

5. The pharmaceutical composition according to claim 2, wherein said nalbuphine polyester is sebacoyl dinalbuphine ester (SDN).

6. The pharmaceutical composition according to claim 1, wherein said oily substance is vegetable oil.

7. The pharmaceutical composition according to claim 6, wherein said vegetable oil is sesame oil.

8. The pharmaceutical composition according to claim 1, wherein said nalbuphine ester is about 1% to 15% by weight of said composition.

9. The pharmaceutical composition according to claim 8, wherein said nalbuphine ester is about 10% by weight of said composition.

10. The pharmaceutical composition according to claim 1, wherein said oily substance is about 30% to 90% by weight of the composition.

11. The pharmaceutical composition according to claim 10, wherein said oily substance is about 55% by weight of the composition.

12. The pharmaceutical composition according to claim 1, wherein said solubility-assisting agent is about 5% to 50% by weight of the composition.

13. The pharmaceutical composition according to claim 12, wherein said solubility-assisting agent is about 45% by weight of the composition.

14. The pharmaceutical composition of claim 1, wherein said pharmaceutical composition is and analgesic.

* * * * *